US007160704B2

(12) United States Patent
Takeshita et al.

(10) Patent No.: US 7,160,704 B2
(45) Date of Patent: Jan. 9, 2007

(54) METHOD FOR PRODUCING TARGET SUBSTANCE

(75) Inventors: Ryo Takeshita, Kawasaki (JP); Hisashi Yasueda, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 209 days.

(21) Appl. No.: 10/792,647

(22) Filed: Mar. 4, 2004

(65) Prior Publication Data

US 2004/0191875 A1 Sep. 30, 2004

(30) Foreign Application Priority Data

Mar. 4, 2003 (JP) ............................ 2003-057171

(51) Int. Cl.
*C12P 13/04* (2006.01)
*C12P 21/04* (2006.01)
*C12N 1/20* (2006.01)
*C12N 15/77* (2006.01)

(52) U.S. Cl. ................ 435/106; 435/252.32; 435/487; 435/70.1; 435/115

(58) Field of Classification Search .............. 435/70.1, 435/115, 487, 106
See application file for complete search history.

(56) References Cited

U.S. PATENT DOCUMENTS

| | | | | |
|---|---|---|---|---|
| 3,616,224 | A | 10/1971 | Shiio et al. | 195/49 |
| 5,217,883 | A | 6/1993 | Anazawa et al. | 435/115 |
| 6,083,728 | A | 7/2000 | Frederick et al. | 435/110 |
| 6,461,852 | B1 | 10/2002 | Tsujimoto et al. | |
| 2003/0013174 | A1 | 1/2003 | Tsujimoto et al. | |
| 2003/0049805 | A1 | 3/2003 | Nagase et al. | |
| 2003/0119155 | A1 | 6/2003 | Yasueda et al. | 435/115 |
| 2003/0124687 | A1 | 7/2003 | Gunji et al. | |
| 2003/0166174 | A1 | 9/2003 | Ono et al. | |
| 2003/0232338 | A1 | 12/2003 | Usuda et al. | |
| 2004/0142435 | A1 | 7/2004 | Gunji et al. | |
| 2004/0146974 | A1 | 7/2004 | Gunji et al. | |
| 2004/0166570 | A1 | 8/2004 | Yasueda et al. | |
| 2004/0170985 | A1 | 9/2004 | Usuda et al. | |
| 2004/0170986 | A1 | 9/2004 | Usuda et al. | |
| 2004/0170987 | A1 | 9/2004 | Usuda et al. | |
| 2004/0171134 | A1 | 9/2004 | Yasueda et al. | |
| 2004/0214296 | A1 | 10/2004 | Asahara et al. | |
| 2004/0229311 | A1 | 11/2004 | Hirano et al. | |
| 2005/0003495 | A1 | 1/2005 | Gunji et al. | |

FOREIGN PATENT DOCUMENTS

| | | |
|---|---|---|
| EP | 1 266 966 A | 12/2002 |
| GB | 2 052 504 A | 1/1981 |
| JP | 50-25790 | 3/1975 |
| WO | WO 99/20783 | 4/1999 |

OTHER PUBLICATIONS

Bastide A., et al. Methanol metabolism in Corynebacterium sp. XG, a facultatively methylotrophic strain, J. Gen. General Microbiology, 1989, 135 (11), 2869-2874; abstract.*

European Search Report Jun. 28, 2004 EPX.

Arfman N. et al., "Methanol metabolism in thermotolerant methylotrophic Bacillus strains involving a novel catabolic NAD-dependent methanol dehydrogenase as a key enzyme", Arch. Microbiol., 1989, vol. 152, pp. 280-288.

Beardsmore A. J. et al., "Characterization of the Assimilatory and Dissimilatory Pathways of Carbon Metabolism during Growth of Methylophilus methylotrophus on Methanol", Journal of General Microbiology, 1982, vol. 128, pp. 1423-1439.

Nesvera J. et al., "Transformation of a new Gram-positive methylotroph, Brevibacterium methylicum, by plasmid DNA", Appl. Microbiol. Biotechnol., 1991, vol. 35, pp. 777-780.

Dijkhuizen L et al., "The Physiology and Biochemistry of Aerobic Methanol-Utilizing Gram-Negative and Gram-Positive Bacteria", Biotechnology Handbooks; Methane and Methanol Utilizers, Plenum Press, 233 Spring Street, New York, USA; 1992, pp. 149-181.

U.S. Appl. No. 09/926299 filed Oct. 9, 2001, Gunji et al.

U.S. Appl. No. 10/791853, filed Mar. 4, 2004, Takeshita et al.

* cited by examiner

*Primary Examiner*—Rebecca E. Prouty
*Assistant Examiner*—Malgorzata A. Walicka
(74) *Attorney, Agent, or Firm*—Shelly Guest Cermak; Cermak & Kenealy LLP

(57) ABSTRACT

The present invention discloses a method for producing a target substance using a coryneform bacterium comprising culturing a coryneform bacterium having an ability to produce the target substance in a medium, resulting in accumulation of the target substance in the medium or cells of the bacterium, and collecting the target substance from the medium or the cells of the bacterium. Also disclosed is a coryneform bacterium which is introduced with a methanol dehydrogenase gene and which has enhanced activities of hexulose phosphate synthase and phosphohexuloisomerase, and to which an ability to utilize methanol is imparted or which has enhanced ability to utilize methanol, and the medium contains methanol as a carbon source.

10 Claims, No Drawings

SEQUENCE LISTING

```
<160> NUMBER OF SEQ ID NOS: 19

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Primer
      MDH-BM-1

<400> SEQUENCE: 1

taaaaaggat ccccgatgat acaacaccaa acgg                              34


<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Primer
      MDH-BM-2

<400> SEQUENCE: 2

gaccgaattc catgtagttt ttcctcattc acc                               33


<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Primer
      sacB-S

<400> SEQUENCE: 3

cgggatcctt tttaacccat caca                                         24
```

-continued

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Primer sacB-R

<400> SEQUENCE: 4
gaagatcttc aaaaggttag gaatacggt 29

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Primer lysI1

<400> SEQUENCE: 5
caaatggaaa atcgggatcg 20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Primer lysI4

<400> SEQUENCE: 6
gtacaccatg atgccgcgca c 21

<210> SEQ ID NO 7
<211> LENGTH: 39
<212> TYPE: DNA
<213> ORGANISM: Artificial Sequence
<220> FEATURE:
<223> OTHER INFORMATION: Description of Artificial Sequence: Primer lysI5

<400> SEQUENCE: 7
tcaggtgcgc ggcatcatgg tgtactgacc caacaagag 39

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Primer lysI2

<400> SEQUENCE: 8
cagcgaaaag atagatggtc 20

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Primer lysI3

<400> SEQUENCE: 9
gctctagacc ctcaaaacat cggctcag 28

-continued

```
<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Primer
      lysI6

<400> SEQUENCE: 10

gctctagagc aaatcctggt ccacacatag                                     30


<210> SEQ ID NO 11
<211> LENGTH: 37
<212> TYPE: DNA
<213> ORGANISM: Artificial Sequence
<220> FEATURE:
<223> OTHER INFORMATION: Description of Artificial Sequence: primer
      Bs-AMD-F1

<400> SEQUENCE: 11

gctttgtttt tttgaattcc aagagacata cagccga                              37


<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: primer
      Bs-AMD-R1

<400> SEQUENCE: 12

cacttttttt tgcaggttga attccgtttc                                     30


<210> SEQ ID NO 13
<211> LENGTH: 39
<212> TYPE: DNA
<213> ORGANISM: Artificial Sequence
<220> FEATURE:
<223> OTHER INFORMATION: Description of Artificial Sequence:
      Bm-RMP-F3-Kpn

<400> SEQUENCE: 13

cttatggtac ctgatggatc attcatacct ttttttccc                            39


<210> SEQ ID NO 14
<211> LENGTH: 39
<212> TYPE: DNA
<213> ORGANISM: Artificial Sequence
<220> FEATURE:
<223> OTHER INFORMATION: Description of Artificial Sequence: primer
      Bm-RMP-R3-Kpn

<400> SEQUENCE: 14

cgcgttggta cctctcccat atggtcgaca ctatataaa                            39


<210> SEQ ID NO 15
<211> LENGTH: 555
<212> TYPE: DNA
<213> ORGANISM: Bacillus subtilis
<220> FEATURE:
<221> NAME/KEY: CDS
<222> LOCATION: (1)..(555)

<400> SEQUENCE: 15

atg aaa tca tta gaa gaa aaa aca att gcc aaa gaa cag att ttt tcg       48
Met Lys Ser Leu Glu Glu Lys Thr Ile Ala Lys Glu Gln Ile Phe Ser
  1               5                  10                  15
```

-continued

```
ggt aaa gtc att gat ctt tat gtc gag gat gta gag ctg cca aac ggc        96
Gly Lys Val Ile Asp Leu Tyr Val Glu Asp Val Glu Leu Pro Asn Gly
             20                  25                  30

aaa gcc agt aaa cgt gaa att gtg aaa cac cct gga gct gta gcg gta       144
Lys Ala Ser Lys Arg Glu Ile Val Lys His Pro Gly Ala Val Ala Val
         35                  40                  45

cta gcc gtc aca gat gaa ggg aaa atc atc atg gtc aaa caa ttc cgt       192
Leu Ala Val Thr Asp Glu Gly Lys Ile Ile Met Val Lys Gln Phe Arg
     50                  55                  60

aag ccg ctt gag cgg acg atc gtt gaa att ccg gcc ggt aag ctt gaa       240
Lys Pro Leu Glu Arg Thr Ile Val Glu Ile Pro Ala Gly Lys Leu Glu
 65                  70                  75                  80

aaa ggt gag gag ccg gag tat acg gca ctt cgg gaa ctt gaa gag gaa       288
Lys Gly Glu Glu Pro Glu Tyr Thr Ala Leu Arg Glu Leu Glu Glu Glu
                 85                  90                  95

acc ggt tat aca gca aaa aaa ctg aca aaa ata act gcg ttt tat aca       336
Thr Gly Tyr Thr Ala Lys Lys Leu Thr Lys Ile Thr Ala Phe Tyr Thr
            100                 105                 110

tca ccc gga ttt gca gat gaa atc gtt cac gtt ttt ctt gct gag gag       384
Ser Pro Gly Phe Ala Asp Glu Ile Val His Val Phe Leu Ala Glu Glu
        115                 120                 125

ctt tct gtg ctt gaa gaa aaa cgg gag ctt gat gag gac gag ttt gtt       432
Leu Ser Val Leu Glu Glu Lys Arg Glu Leu Asp Glu Asp Glu Phe Val
    130                 135                 140

gaa gtg atg gag gtg acg ctt gaa gat gcg cta aag ctg gtt gaa tcg       480
Glu Val Met Glu Val Thr Leu Glu Asp Ala Leu Lys Leu Val Glu Ser
145                 150                 155                 160

cgt gaa gta tat gat gct aaa aca gcc tac gcg att cag tat ctt cag       528
Arg Glu Val Tyr Asp Ala Lys Thr Ala Tyr Ala Ile Gln Tyr Leu Gln
                165                 170                 175

ctg aaa gaa gcg ctc caa gca caa aaa                                   555
Leu Lys Glu Ala Leu Gln Ala Gln Lys
            180                 185


<210> SEQ ID NO 16
<211> LENGTH: 185
<212> TYPE: PRT
<213> ORGANISM: Bacillus subtilis

<400> SEQUENCE: 16

Met Lys Ser Leu Glu Glu Lys Thr Ile Ala Lys Glu Gln Ile Phe Ser
  1               5                  10                  15

Gly Lys Val Ile Asp Leu Tyr Val Glu Asp Val Glu Leu Pro Asn Gly
             20                  25                  30

Lys Ala Ser Lys Arg Glu Ile Val Lys His Pro Gly Ala Val Ala Val
         35                  40                  45

Leu Ala Val Thr Asp Glu Gly Lys Ile Ile Met Val Lys Gln Phe Arg
     50                  55                  60

Lys Pro Leu Glu Arg Thr Ile Val Glu Ile Pro Ala Gly Lys Leu Glu
 65                  70                  75                  80

Lys Gly Glu Glu Pro Glu Tyr Thr Ala Leu Arg Glu Leu Glu Glu Glu
                 85                  90                  95

Thr Gly Tyr Thr Ala Lys Lys Leu Thr Lys Ile Thr Ala Phe Tyr Thr
            100                 105                 110

Ser Pro Gly Phe Ala Asp Glu Ile Val His Val Phe Leu Ala Glu Glu
        115                 120                 125

Leu Ser Val Leu Glu Glu Lys Arg Glu Leu Asp Glu Asp Glu Phe Val
    130                 135                 140
```

-continued

```
Glu Val Met Glu Val Thr Leu Glu Asp Ala Leu Lys Leu Val Glu Ser
145                 150                 155                 160

Arg Glu Val Tyr Asp Ala Lys Thr Ala Tyr Ala Ile Gln Tyr Leu Gln
                165                 170                 175

Leu Lys Glu Ala Leu Gln Ala Gln Lys
            180                 185


<210> SEQ ID NO 17
<211> LENGTH: 1823
<212> TYPE: DNA
<213> ORGANISM: Bacillus brevis
<220> FEATURE:
<221> NAME/KEY: CDS
<222> LOCATION: (508)..(1140)
<220> FEATURE:
<221> NAME/KEY: CDS
<222> LOCATION: (1149)..(1700)

<400> SEQUENCE: 17

agccaatgac ggaaaatgat tgaggcattt tttgatccag aaataaatta tacaaagcag      60

gatagatttt ccttttagct aaatcccctg tcgcgccaaa caagacaaag gtcatcgaat     120

ccacttttca tacctccaca ttaacatttg ttgcggcaaa tattagtata atatgtatat     180

tttttatatg taagtacgca cttattaatc ttatagttac aaatttatat aaagtataaa     240

taatatacta taaaaaatct tatggaaagt gatggatcat tcatacccttt ttttcccgta    300

ttgtttacat tttctatagg aattttttct taatagtata ctttttatac tatgtgttaa     360

taaagtgcgt actttttaaa aaatttgata gatagtatat taacagtgta caggcaaaag     420

aaggaataca cacatttgct tgtacaatac aaagttacat aattgtaaca aaaaaaacta     480

aaaattttga aaaggagtgt ataattt atg caa ctt caa tta gct cta gat ttg     534
                              Met Gln Leu Gln Leu Ala Leu Asp Leu
                              1               5

gta aac att gaa gaa gca aaa caa gta gta gct gag gtt cag gag tat      582
Val Asn Ile Glu Glu Ala Lys Gln Val Val Ala Glu Val Gln Glu Tyr
10                  15                  20                  25

gtc gat atc gta gaa atc ggt act ccg gtt att aaa att tgg ggt ctt      630
Val Asp Ile Val Glu Ile Gly Thr Pro Val Ile Lys Ile Trp Gly Leu
                30                  35                  40

caa gct gta aaa gaa gtt aaa gac gca ttc cct cat tta caa gtt tta      678
Gln Ala Val Lys Glu Val Lys Asp Ala Phe Pro His Leu Gln Val Leu
            45                  50                  55

gct gac atg aaa act atg gat gct gca gca tat gaa gtt gct aaa gca      726
Ala Asp Met Lys Thr Met Asp Ala Ala Ala Tyr Glu Val Ala Lys Ala
        60                  65                  70

gct gag cat ggc gct gat atc gta aca att ctt gca gca gct gaa gat      774
Ala Glu His Gly Ala Asp Ile Val Thr Ile Leu Ala Ala Ala Glu Asp
    75                  80                  85

gta tca att aag ggt gct gta gaa gaa gcg aaa aaa ctt ggc aaa aaa      822
Val Ser Ile Lys Gly Ala Val Glu Glu Ala Lys Lys Leu Gly Lys Lys
90                  95                  100                 105

atc ctt gtt gac atg atc gca gtt aaa aat tta gaa gag cgt gca aaa      870
Ile Leu Val Asp Met Ile Ala Val Lys Asn Leu Glu Glu Arg Ala Lys
                110                 115                 120

caa gtg gat gaa atg ggt gta gac tac att tgt gtt cac gct gga tac      918
Gln Val Asp Glu Met Gly Val Asp Tyr Ile Cys Val His Ala Gly Tyr
            125                 130                 135

gat ctc caa gca gta ggt aaa aac cca tta gat gat ctt aag aga att      966
Asp Leu Gln Ala Val Gly Lys Asn Pro Leu Asp Asp Leu Lys Arg Ile
        140                 145                 150
```

-continued

```
aaa gct gtc gtg aaa aat gca aaa act gct att gca ggc gga atc aaa      1014
Lys Ala Val Val Lys Asn Ala Lys Thr Ala Ile Ala Gly Gly Ile Lys
    155                 160                 165

tta gaa aca ttg cct gaa gtt atc aaa gca gaa ccg gat ctt gtc att      1062
Leu Glu Thr Leu Pro Glu Val Ile Lys Ala Glu Pro Asp Leu Val Ile
170                 175                 180                 185

gtc ggc ggc ggt att gct aac caa act gat aaa aaa gca gca gct gaa      1110
Val Gly Gly Gly Ile Ala Asn Gln Thr Asp Lys Lys Ala Ala Ala Glu
                190                 195                 200

aaa ata aat aaa tta gtt aaa caa ggg tta tgatcagc atg cag aca act     1160
Lys Ile Asn Lys Leu Val Lys Gln Gly Leu          Met Gln Thr Thr
            205                 210              1

gaa ttc tta tct gaa atc gta aaa gaa tta agt aat tcg gtt aac caa      1208
Glu Phe Leu Ser Glu Ile Val Lys Glu Leu Ser Asn Ser Val Asn Gln
5                   10                  15                  20

atc gcc gat gaa gaa gcg gaa gca ctg gta aac gga att ctt caa tca      1256
Ile Ala Asp Glu Glu Ala Glu Ala Leu Val Asn Gly Ile Leu Gln Ser
                25                  30                  35

aag aaa gta ttt gtt gcc ggt gca gga aga tcc ggt ttt atg gca aaa      1304
Lys Lys Val Phe Val Ala Gly Ala Gly Arg Ser Gly Phe Met Ala Lys
            40                  45                  50

tcc ttt gcg atg cgc atg atg cac atg gga att gat gcc tat gtc gtt      1352
Ser Phe Ala Met Arg Met Met His Met Gly Ile Asp Ala Tyr Val Val
        55                  60                  65

ggc gaa acc gta act cct aac tat gaa aaa gaa gac att tta att att      1400
Gly Glu Thr Val Thr Pro Asn Tyr Glu Lys Glu Asp Ile Leu Ile Ile
     70                  75                  80

gga tcc ggc tct gga gaa aca aaa ggt ctc gtt tcc atg gct caa aaa      1448
Gly Ser Gly Ser Gly Glu Thr Lys Gly Leu Val Ser Met Ala Gln Lys
85                  90                  95                  100

gca aaa agc ata ggt gga acc att gcg gct gta acg att aat cct gaa      1496
Ala Lys Ser Ile Gly Gly Thr Ile Ala Ala Val Thr Ile Asn Pro Glu
                105                 110                 115

tca aca atc gga caa tta gcg gat atc gtt att aaa atg cca ggt tcg      1544
Ser Thr Ile Gly Gln Leu Ala Asp Ile Val Ile Lys Met Pro Gly Ser
            120                 125                 130

cct aaa gat aaa tca gaa gca agg gaa act att caa cca atg gga tcc      1592
Pro Lys Asp Lys Ser Glu Ala Arg Glu Thr Ile Gln Pro Met Gly Ser
        135                 140                 145

ctt ttc gag caa aca tta tta tta ttc tat gat gct gtc att ttg aga      1640
Leu Phe Glu Gln Thr Leu Leu Leu Phe Tyr Asp Ala Val Ile Leu Arg
    150                 155                 160

ttc atg gag aaa aaa ggc ttg gat aca aaa aca atg tac gga aga cat      1688
Phe Met Glu Lys Lys Gly Leu Asp Thr Lys Thr Met Tyr Gly Arg His
165                 170                 175                 180

gcc aat ctc gag taggcgtgga attaagaaaa ggaagaccgc gatgctttgc          1740
Ala Asn Leu Glu

ggtctttcct tgttttttt acattacatg atgtttatat agtgtcgacc atatgggaga     1800

gctcccaacg cgttggatgc ata                                            1823
```

<210> SEQ ID NO 18
<211> LENGTH: 211
<212> TYPE: PRT
<213> ORGANISM: Bacillus brevis

<400> SEQUENCE: 18

```
Met Gln Leu Gln Leu Ala Leu Asp Leu Val Asn Ile Glu Glu Ala Lys
  1               5                  10                  15

Gln Val Val Ala Glu Val Gln Glu Tyr Val Asp Ile Val Glu Ile Gly
```

-continued

```
            20                  25                  30

Thr Pro Val Ile Lys Ile Trp Gly Leu Gln Ala Val Lys Glu Val Lys
        35                  40                  45

Asp Ala Phe Pro His Leu Gln Val Leu Ala Asp Met Lys Thr Met Asp
    50                  55                  60

Ala Ala Ala Tyr Glu Val Ala Lys Ala Ala Glu His Gly Ala Asp Ile
 65                  70                  75                  80

Val Thr Ile Leu Ala Ala Ala Glu Asp Val Ser Ile Lys Gly Ala Val
                85                  90                  95

Glu Glu Ala Lys Lys Leu Gly Lys Lys Ile Leu Val Asp Met Ile Ala
            100                 105                 110

Val Lys Asn Leu Glu Glu Arg Ala Lys Gln Val Asp Glu Met Gly Val
        115                 120                 125

Asp Tyr Ile Cys Val His Ala Gly Tyr Asp Leu Gln Ala Val Gly Lys
    130                 135                 140

Asn Pro Leu Asp Asp Leu Lys Arg Ile Lys Ala Val Val Lys Asn Ala
145                 150                 155                 160

Lys Thr Ala Ile Ala Gly Gly Ile Lys Leu Glu Thr Leu Pro Glu Val
                165                 170                 175

Ile Lys Ala Glu Pro Asp Leu Val Ile Val Gly Gly Gly Ile Ala Asn
            180                 185                 190

Gln Thr Asp Lys Lys Ala Ala Ala Glu Lys Ile Asn Lys Leu Val Lys
        195                 200                 205

Gln Gly Leu
    210


<210> SEQ ID NO 19
<211> LENGTH: 184
<212> TYPE: PRT
<213> ORGANISM: Bacillus brevis

<400> SEQUENCE: 19

Met Gln Thr Thr Glu Phe Leu Ser Glu Ile Val Lys Glu Leu Ser Asn
  1               5                  10                  15

Ser Val Asn Gln Ile Ala Asp Glu Glu Ala Glu Ala Leu Val Asn Gly
            20                  25                  30

Ile Leu Gln Ser Lys Lys Val Phe Val Ala Gly Ala Gly Arg Ser Gly
        35                  40                  45

Phe Met Ala Lys Ser Phe Ala Met Arg Met Met His Met Gly Ile Asp
    50                  55                  60

Ala Tyr Val Val Gly Glu Thr Val Thr Pro Asn Tyr Glu Lys Glu Asp
 65                  70                  75                  80

Ile Leu Ile Ile Gly Ser Gly Ser Gly Glu Thr Lys Gly Leu Val Ser
                85                  90                  95

Met Ala Gln Lys Ala Lys Ser Ile Gly Gly Thr Ile Ala Ala Val Thr
            100                 105                 110

Ile Asn Pro Glu Ser Thr Ile Gly Gln Leu Ala Asp Ile Val Ile Lys
        115                 120                 125

Met Pro Gly Ser Pro Lys Asp Lys Ser Glu Ala Arg Glu Thr Ile Gln
    130                 135                 140

Pro Met Gly Ser Leu Phe Glu Gln Thr Leu Leu Leu Phe Tyr Asp Ala
145                 150                 155                 160
```

-continued

```
Val Ile Leu Arg Phe Met Glu Lys Lys Gly Leu Asp Thr Lys Thr Met
                165                 170                 175

Tyr Gly Arg His Ala Asn Leu Glu
            180
```

METHOD FOR PRODUCING TARGET SUBSTANCE

BACKGROUND OF THE INVENTION

1. Field of the Invention

The present invention relates to the microbial fermentation industry. More specifically, the present invention relates to a technique for imparting an ability to utilize methanol to a microorganism not inherently having such an ability or enhancing such an ability of a microorganism having such an ability at a low level, and a method for producing a target substance by utilizing methanol with use of a microorganism obtained by such a technique as mentioned above.

Substances produced according to the present invention include L-amino acids, nucleic acids, antibiotics, vitamins, growth factors, physiologically active substances and so forth, which have conventionally been produced utilizing microorganisms.

2. Brief Description of the Related Art

To date, most fermentation raw materials utilized in production of useful substances by microbial fermentation are sugars derived from agricultural products. However, since the price of sugars derived from agricultural products have been reported to be on an upward trend, an inexpensive material of good quality is desirable as an alternative fermentation raw material.

Methanol is easily dissolved in water and inexpensive, and it can be obtained at a high purity level. Moreover, it can be comparatively easily produced from methane, which is a main component of natural gas. Therefore it is preferable as a raw material for substance production. If methanol is used as a raw material for microbial fermentation, not only the cost of the principal raw material can be reduced, but also purification of products from fermentation solutions and waste solution disposal processes can be simplified. Thus, the total production cost can be reduced. Methods for producing substances, particularly amino acids, using methanol as a raw material utilizing microorganisms are known, and include a method of utilizing a microorganism of the genus *Achromobacter* or *Pseudomonas* (Japanese Patent Publication (Kokoku) No. 45-25273), a method of utilizing a microorganism of the genus *Protaminobacter* or *Methanomonas* (Japanese Patent Laid-open Publication (Kokai) No. 50-25790), a method of utilizing a microorganism of the genus *Methylobacillus* (Japanese Patent Laid-open Publication No. 4-91793), a method of utilizing a methylotrophic bacterium belonging to the genus *Bacillus* (Japanese Patent Laid-open Publication No. 3-505284, U.S. Pat. No. 6,083,728) and so forth. However, known bacterial strains have not acquired high productivity of amino acids necessary for bacteria for practical use.

Meanwhile, methods of utilizing microorganisms of the genus *Brevibacterium, Corynebacterium, Bacillus* or *Escherichia* have constituted the mainstream of amino acid production from glucose (see "Amino Acid Fermentation", Ed. By H. Aida et al., the Japan Scientific Societies Press [Gakkai Shuppan Center], 1 st Edition, published on May 30, 1986)). These amino acid-producing bacteria are precious bacterial strains bred by introducing various mutations so that the maximum amino acid productivity is obtained while further breeding is refined for practical use. However, this can be a long time. Furthermore, these industrially-used strains cannot utilize methanol.

SUMMARY OF THE INVENTION

An object of the present invention is to provide a novel coryneform bacterium which has an ability to produce a fermentation product such as an amino acid from methanol as a fermentation raw material by imparting an ability to utilize methanol to a coryneform bacterium that is inherently can utilize a sugar, but cannot utilize methanol, or by enhancing such an ability of a bacterium having an existing ability, but at a low level. It is a further object of the present invention to provide a method for producing a target substance from methanol utilizing such a bacterium.

It is an object of the present invention to provide a method for producing a target substance using a coryneform bacterium comprising:

(A) culturing a coryneform bacterium having an ability to produce the target substance in a medium, resulting in accumulation of the target substance in the medium or cells of the bacterium, and (B) collecting the target substance from the medium or the cells of the bacterium, wherein a methanol dehydrogenase gene, hexulose phosphate synthase gene and phosphohexuloisomerase gene are introduced into the coryneform bacterium, and the bacterium is modified so that an ability to utilize methanol is imparted, and the medium contains methanol as a carbon source.

It is a further object of the present invention to provide the method as described above, wherein the bacterium is further introduced with a gene encoding a methanol dehydrogenase activity promoting factor.

It is a further object of the present invention to provide the method as described above, wherein the target substance is an L-amino acid.

It is a further object of the present invention to provide the method as described above, wherein the L-amino acid is L-lysine.

It is a further object of the present invention to provide the method as described above, wherein the bacterium belongs to the genus *Corynebacterium.*

It is a further object of the present invention to provide the method as described above, wherein the coryneform bacterium is *Corynebacterium glutamicum.*

It is a further object of the present invention to provide a coryneform bacterium which is introduced with a methanol dehydrogenase gene, hexulose phosphate synthase gene and phosphohexuloisomerase gene, and which is modified so that an ability to utilize methanol is imparted.

It is a still further object of the present invention to provide the coryneform bacterium as described above, which is further introduced with a gene encoding a methanol dehydrogenase activity promoting factor.

It is even a further object of the present invention to provide the coryneform bacterium as described above, which belongs to the genus *Corynebacterium.*

It is a further object of the present invention to provide the coryneform bacterium as described above, which is *Corynebacterium glutamicum.*

According to the present invention, an ability to utilize methanol can be imparted to a coryneform bacterium that cannot naturally utilize methanol, and thus there can be provided a microorganism that can utilize inexpensive methanol as a carbon source or energy source utilized by the coryneform bacterium. Further, by utilizing the obtained microorganism, various fermentation products can be produced from methanol added to a medium.

DESCRIPTION OF PREFERRED EMBODIMENTS

The inventors of the present invention assiduously studied in order to achieve the aforementioned objects. As a result, they found that, by introducing genes encoding hexulose phosphate synthase and phosphohexuloisomerase as well as a methanol dehydrogenase gene into a coryneform bacterium, to express these genes in the bacterium, an ability to utilize methanol can be imparted to the bacterium, or the ability of the bacterium can be enhanced, and thus accomplished the present invention.

Hereinafter, the present invention will be explained in detail.

The coryneform bacterium of the present invention is a bacterium which has a gene encoding a methanol dehydrogenase introduced into it, along with the introduction of further genes encoding hexulose phosphate synthase and phosphohexuloisomerase, and which is modified so that an ability to utilize methanol is imparted or enhanced.

A microorganism that can utilize methanol has a methanol oxidase (e.g., methanol dehydrogenase) and it dissimilates or assimilates formaldehyde produced by oxidation of methanol through precise metabolic regulation. This is because formaldehyde is strongly toxic for organisms and therefore cells must rapidly utilize it as a carbon source or energy source or dispose it by detoxification. On the other hand, if it is desired to impart an ability to utilize methanol to a microorganism that cannot utilize methanol, it is absolutely necessary to introduce a methanol oxidase. However, there are scarcely specific measures for proper disposal of formaldehyde produced due to expression of the methanol oxidase activity, and therefore it has been considered that it is impossible to impart an ability to utilize methanol to an arbitrary microorganism.

However, the inventors of the present invention found that the ability to utilize methanol could be imparted even to a microorganism that inherently cannot utilize methanol, particularly coryneform bacterium, if an enzyme having methanol oxidation ability was to exist in cells of the microorganism, as well as genes encoding hexulose phosphate synthase and phosphohexuloisomerase simultaneously introduced into the microorganism, to express these genes.

The coryneform bacterium of the present invention is not particularly limited, so long as the aforementioned properties can be imparted to the bacterium. Coryneform bacteria include those bacteria having been previously classified into the genus *Brevibacterium*, but currently united into the genus *Corynebacterium* (Int. J. Syst. Bacteriol., 41, 255 (1981)), and include bacteria belonging to the genus *Brevibacterium* which is a close relative of the genus *Corynebacterium*. Examples of such coryneform bacteria are as follows.

*Corynebacterium acetoacidophilum*
*Corynebacterium acetoglutamicum*
*Corynebacterium alkanolyticum*
*Corynebacterium callunae*
*Corynebacterium glutamicum*
*Corynebacterium lilium* (*Corynebacterium glutamicum*)
*Corynebacterium melassecola*
*Corynebacterium thermoaminogenes*
*Corynebacterium herculis*
*Brevibacterium divaricatum* (*Corynebacterium glutamicum*)
*Brevibacteriumflavum* (*Corynebacterium glutamicum*)
*Brevibacterium immariophilum*
*Brevibacterium lactofermentum* (*Corynebacterium glutamicum*)
*Brevibacterium roseum*
*Brevibacterium saccharolyticum*
*Brevibacterium thiogenitalis*
*Brevibacterium album*
*Brevibacterium cerinum*
*Microbacterium ammoniaphilum*

Specifically, examples of the bacterium include *Corynebacterium acetoacidophilum* AJ12318 (FERM BP-1172, see U.S. Pat. No. 5,188,949) etc. for L-threonine producer; *Brevibacterium lactofermentum* AJ12435 (FERM BP-2294, U.S. Pat. No. 5,304,476), *Brevibacterium lactofermentum* AJ3990 (ATCC 31269, see U.S. Pat. No. 4,066,501) and AJ110135 described later etc. for L-lysine producer; *Brevibacterium lactofermentum* AJ12821 (FERM BP-4172, Japanese Patent Laid-open Publication No. 5-26811, French Patent Laid-open Publication No. 2,701,489), *Brevibacterium lactofermentum* AJ12475 (FERM BP-2922, see U.S. Pat. No. 5,272,067), *Brevibacterium lactofermentum* AJ13029 (FERM BP-5189, see International Patent Publication JP95/01586) etc. for L-glutamic acid producer; *Brevibacterium lactofermentum* AJ3718 (FERM P-2516, see U.S. Pat. No. 3,970,519) etc. for L-leucine producer; *Brevibacterium flavum* AJ12149 (FERM BP-759, see U.S. Pat. No. 4,656,135) etc. for L-isoleucine producer; *Brevibacterium lactofermentum* AJ12341 (FERM BP-1763, see U.S. Pat. No. 5,188,948) etc. for L-valine producer; *Brevibacterium lactofermentum* AJ12637 (FERM BP-4160, see French Patent Laid-open Publication No. 2,686,898) etc. for L-phenylalanine producer.

As a result of assiduous studies, the inventors of the present invention conceived of obtaining sufficient methanol dehydrogenase activity in cells and enhancement of a function for assimilating formaldehyde produced by the enzymatic reaction at the same time as fundamental conditions for imparting the ability to utilize methanol. The inventors of the present invention further conceived that enhancement of enzymatic activities of hexulose phosphate synthase (HPS) and phosphohexuloisomerase (PHI), which are key enzymes of the ribulose monophosphate pathway, would be effective for effective assimilation of formaldehyde. Thus, they found that the ability to utilize methanol could be imparted to a coryneform bacterium that inherently could not utilize methanol, by introducing into the coryneform bacterium genes encoding HPS and PHI together with a methanol dehydrogenase gene.

The methanol dehydrogenase (MDH) used for the present invention is an enzyme having an enzymatic activity that can oxidize methanol to convert it into formaldehyde. An example of MDH that can be used for the present invention includes, but is not limited to, PQQ (pyrroloquinolinequinone) dependent-type MDH, which is mainly seen in Gram-negative bacteria. Specifically, MDH of *Methylobacterium extorquens* AM1 strain (Biochim. Biophys. Acta, 1119:97–106 (1992)) etc. is encompassed. Further, NAD (nicotinamide adenine dinucleotide) dependent-type MDH seen in Gram positive bacteria, specifically, MDH of *Bacillus methanoliocus* (J. Bacteriol., 174:5346–5353 (1992)), alcohol dehydrogenase (ADH) derived from *Bacillus stearothermophilus* DSM 2334 strain (Biochem. J., 252:661–666) etc. are encompassed by the present invention. Furthermore, ADH in bovine liver (Biochem. J., 100:34–46 (1966)) and human liver (Arch. Toxicol., 72:604–607 (1998)) are also encompassed. Further, a mutant-type alcohol dehydrogenase that acts on methanol can also be newly created by introducing a mutation into a gene of alcohol dehydrogenase that inherently does not act on methanol, to modify its substrate specificity, and used. However, as MDH that can be suitably used for the present invention, MDH derived from, for example, *Bacillus brevis* NCIMB No. 12524, which is a methanol-assimilating bacterium belonging to the genus Bacillus, is encompassed.

A gene encoding MDH (mdh) can be obtained from a microorganism that produces MDH using usual gene-cloning methods. For example, an MDH gene can be obtained by PCR (polymerase chain reaction) using chromosomal DNA of *Bacillus brevis* S1 strain (NCIMB 12524) as a template and oligonucleotides having the nucleotide sequences shown in SEQ ID NOS: 1 and 2 as primers. Methods for preparation of the genomic DNA library used for gene cloning, hybridization, PCR, preparation of plasmid DNA, digestion and ligation of DNA, transformation etc. are described in Sambrook, J., Fritsch, E. F., Maniatis, T., Molecular Cloning, Cold Spring Harbor Laboratory Press, 1.21 (1989). In addition, whether a MDH gene functions in a coryneform bacterium to which the gene is introduced can be confirmed by measuring MDH activity of the bacterium lysate. The MDH activity can be measured by, for example, a method of measuring reduction of $NAD^+$(nicotinamide adenine dinucleotide) accompanying the oxidation of methanol into formaldehyde through measurement of absorbance at a wavelength of 340 nm.

Specific examples of the mdh gene used for the present invention include, but are not limited to mdh gene of *Bacillus brevis* S1 strain. The mdh gene of *Bacillus methanolicus* C1 strain (NCIMB 13114, Eur. J. Biochem., 244: 426–433 (1997)) has been registerd in GenBank under Accession M65004 (entry name of BACMDH).

In addition, there has been reported the existence of factors for activating activity of methanol dehydrogenase (Amd: Activator of methanol dehydrogenase), such as activator for methanol dehydrogenase of *Bacillus methanolicus* C1 strain (Eur. J. Biochem., 244:426–433 (1997)) and the YqkG gene product of *Bacillus subtilis* 168 strain (Japanese Patent Laid-open Publication No. 2000-69976). These factors are effective means for enhancing activity of MDH. MDH activity in cells of the bacterium can be enhanced by introducing DNA encoding any of these MDH activators (amd gene) into a coryneform bacterium harboring an MDH gene. A gene encoding Amd (amd) such as the YqkG gene can be obtained from chromosomal DNA of *Bacillus subtilis* such as the *Bacillus subtilis* 168 strain by PCR using the chromosomal DNA as a template and primers having the nucleotide sequences shown in SEQ ID NOS: 11 and 12 in Sequence Listing.

As a specific example of the yqkG gene used for the present invention, the YqkG gene of *Bacillus subtilis* 168 strain is encompassed. The nucleotide sequence and the amino acid sequence encoded by this gene are shown in SEQ ID NOS: 15 and 16.

Methods for expressing the activities of HPS and PHI in a bacterium will be explained herein.

In order to express HPS or PHI activity in a target coryneform bacterium, a gene encoding HPS (hps) or PHI (phi) can be ligated to a vector which functions in the target bacterium, preferably a multi-copy type vector, to prepare a recombinant DNA, and used to transform the target bacterium. The copy number of the hps gene or phi gene in the cell of the transformant is thereby increased, and as a result, either of the enzymatic activities is increased.

The hps or phi gene can be obtained from a microorganism that produces HPS or PHI by usual gene cloning methods, similar to the MDH gene.

As the microorganism that produces HPS, *Methylomonas capsulatus* (J. R. Quayle, Methods in Enzymology, 188, p.314, 1990), Methylomonas M15 strain (Methods in Enzymology, 188, p.319, 1990), *Methylomonas aminofaciens* 77*a* strain (Biochim. Biophys. Acta., 523, p.236, 1978), *Mycobacterium gastri* MB19 (Methods in Enzymology, 188, p.393, 1990), *Acetobacter methanolicus* MB58 (Methods in Enzymology, 188, p.401, 1990) etc. are known. Further, as the microorganism that produces PHI, *Methylomonas aminofaciens* 77*a* strain (Agric. Biol. Chem., 41 (7), p1133, 1977), *Mycobacterium gastri* (Japanese Patent Laid-open Publication No. 11-127869), which is a Gram positive facultative methanol-assimilating bacterium, etc. are known. Further, both the hps and phi genes of *Bacillus subtilis* have been reported (J. Bacteriol., 181:7154–7160 (1999)). Furthermore, it has been reported that, in the *Bacillus brevis* S1 strain, which is a methanol-assimilating bacterium belonging to the genus Bacillus, the hps gene and phi gene exist in tandem on chromosomal DNA (Annual Meeting of the Society for Fermentation and Bioengineering Japan, Lecture Abstracts, p. 113 (2000); FEMS Microbiology Letters, 214, 189–193, 2002). A DNA fragment containing the hps and phi genes can be obtained by PCR using chromosomal DNA of the S1 strain as a template and oligonucleotides having the nucleotide sequences shown in SEQ ID NOS: 13 and 14 as primers.

Specific examples of the hps gene and phi gene used for the present invention include the hps gene and phi gene of *Bacillus subtilis* 168 strain and the hps and phi gene of *Bacillus brevis* S1 strain. The nucleotide sequence of the DNA fragment comprising the hps and phi genes of *Bacillus brevis* S1 strain is shown in SEQ ID NO: 17. The amino acid sequences encoded by the genes are shown in SEQ ID NOS: 18 and 19, respectively.

*Bacillus methanolicus* PB1 strain (NCIMB 13113) and *Bacillus brevis* S1 strain (NCIMB 12524) can be obtained from National Collections of Industrial and Marine Bacteria, Address: NCIMB Lts., Torry Research Stationl 35, Abbey Road, Aberdeen AB9 8DG, United Kingdom).

The HPS activity can be measured by the method described in Methods in Enzymology, 188, 397–401 (1990). Further, the PHI activity can be measured by the method described in Journal of Bacteriology, 181, p.7154–7160 (1999).

Amplification of the HPS, PHI, MDH, or AMD activity can also be achieved by introducing multiple copies of their respective genesinto chromosomal DNA of a target coryneform bacterium. To introduce multiple copies of the hps gene or phi gene into chromosomal DNA of a target coryneform bacterium, homologous recombination is carried out using a sequence whose multiple copies exist in the chromosomal DNA as a target. As sequences whose multiple copies exist in chromosomal DNA, repetitive DNA or inverted repeat existing at the end of a transposable element can be used. Further, as disclosed in Japanese Patent Laid-open Publication No. 2-109985, it is also possible to incorporate the hps gene or phi gene into transposon, and allow it to be transferred to introduce multiple copies of the genes into chromosomal DNA. According to any of these methods, the HPS or PHI activity is increased as a result of an increase of copy numbers of the hps gene or phi gene in the transformant strain.

Beside the aforementioned gene amplification, increasing HPS or PHI activity can also be attained by replacing an expression regulatory sequence such as a promoter of the hps gene or phi gene with a stronger one (refer to Japanese Patent Laid-open Publication No. 1-215280). Examples of strong promoters include lac promoter, trp promoter, trc promoter, tac promoter, $P_R$ promoter and $P_L$ promoter of lambda phage, tet promoter, amyE promoter, veg promoter and so forth. Substitution of these promoters enhances expression of the hps gene or phi gene, and thus the HPS or PHI activity is increased. The enhancement of an expression regulatory sequence may be combined with an increase of the copy number of HPS or PHI.

The mdh, hps, phi and amd genes used for the present invention are not limited to wild-type genes, but the present invention also encompassses a mutant or artificially modified gene encoding a gene product including substitution, deletion, insertion, addition or inversion of one or several amino acids at one or more sites, so long as the function of the encoded MDH, HPS, PHI or Amd protein is not diminished. Although the number of "several" amino acids referred to herein differs depending on position or type of amino acid residues in a three-dimensional structure of a protein, it may be specifically 2 to 20, preferably 2 to 10, more preferably 2 to 5.

Furthermore, as DNA encoding a protein substantially identical to the MDH protein, the present invention encompasses DNA hybridizable with a nucleotide sequence registered in GenBank under Accession M65004 (entry name of BACMDH) or a probe that can be produced from the nucleotide sequence under stringent conditions and encodes a protein having an activity similar to that of MDH.

As DNA encoding a protein substantially identical to the aforementioned Amd protein, the present invention encompasses DNA hybridizable with a nucleotide sequence comprising the nucleotide numbers 1 to 555 in SEQ ID NO: 15 or a probe that can be produced from the nucleotide sequence under stringent conditions and encodes a protein having an activity similar to that of Amd.

As DNA encoding a protein substantially identical to the HPS protein, the present invention encompasses DNA hybridizable with a nucleotide sequence comprising the nucleotide numbers 508 to 1140 in SEQ ID NO: 17 or a probe that can be produced from the nucleotide sequence under stringent conditions and encodes a protein having an activity similar to that of HPS.

Further, as DNA encoding a protein substantially identical to the PHI protein, the present invention encompasses DNA hybridizable with a nucleotide sequence comprising the nucleotide numbers 1149 to 1700 in SEQ ID NO: 17 or a probe that can be produced from the nucleotide sequence under stringent conditions and encodes a protein having an activity similar to that of PHI.

"Stringent conditions" mean conditions under which a so-called specific hybrid is formed, and a non-specific hybrid is not formed. It is difficult to clearly express this condition using any numerical value. However, stringent conditions include conditions under which DNAs having high homology, for example, DNAs having homology of 50% or more, preferably 80% or more, more preferably 90% or more, most preferably 95% more hybridize with each other, but DNAs having homology lower than the above do not hybridize with each other. Alternatively, the stringent conditions include conditions whereby DNAs hybridize with each other at a salt concentration corresponding to a typical washing condition of Southern hybridization, i.e., approximately 1×SSC, 0.1% SDS, preferably 0.1×SSC, 0.1% SDS, at 60° C.

To introduce the various genes that can be obtained as described above into a coryneform bacterium, for instance, a method of treating recipient cells with calcium chloride so as to increase the permeability for DNA, which has been reported for *Escherichia coli* K-12 (Mandel, M. and Higa, A., J. Mol. Biol., 53, 159 (1970)), and a method of preparing competent cells from cells which are at growth phase, followed by introduction of the DNA thereinto, which has been reported for *Bacillus subtilis* (Duncan, C. H., Wilson, G. A. and Young, F. E., Gene, 1, 153 (1977)) can be used. In addition to these, a method of making DNA-recipient cells into protoplasts or spheroplasts, which can easily take up a recombinant DNA, followed by introducing a recombinant DNA into the cells, which is known to be applicable to *Bacillus subtilis*, actinomycetes and yeasts (Chang, S. and Choen, S. N., Molec. Gen. Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Sci., USA, 75, 1929 (1978)) can also be used. Furthermore, an electroporation method can be used (Canadian Journal of Microbiology, 43, 197 (1997)). Any of these methods can be suitably selected depending on the cells used as a recipient.

In the coryneform bacterium of the present invention, depending on the type of the target substance, activity of an enzyme involved in the biosynthesis of the target substance may be enhanced. Further, activity of an enzyme disadvantageous for the production of the target substance may be reduced or eliminated.

When the mdh, hps, phi genes, and amd gene as required, are introduced into a coryneform bacterium, the order of the introduction of the genes is not particularly limited. Further, the bacterium of the present invention can be obtained either by introducing these genes into a coryneform bacterium having an ability to produce a target substance, or by imparting an ability to produce a target substance to a coryneform bacterium introduced with these genes.

The coryneform bacterium of the present invention may be a bacterium that has been bred by introducing DNA having genetic information involved in biosynthesis of a target substance using a gene recombination technique. For example, as for L-lysine producing bacteria, examples of genes that can be introduced include genes encoding enzymes of the biosynthetic pathway of L-lysine such as phosphoenolpyruvate carboxylase, aspartokinase, dihydrodipicolinate synthetase, dihydrodipicolinate reductase, succinyldiaminopimelate transaminase and succinyldiaminopimelate deacylase. In the case of a gene encoding an enzyme which is subject to feedback inhibition by L-aspartic acid or L-lysine such as phosphoenolpyruvate carboxylase or aspartokinase and dihydrodipicolinate synthetase, it is desirable to use a mutant gene encoding an enzyme for which inhibition is desensitized. An example of a mutant lysC gene (lysC*) encoding a mutant aspartokinase for which inhibition is desensitized includes the gene harbored by the L-lysine producing bacterium AJ3463 (FERM P-1987) derived from the *Brevibacterium lactofermentum* ATCC 13869 strain by a mutation treatment (International Patent Publication WO94/25605).

Further, in the coryneform bacterium of the present invention, an activity of an enzyme that catalyzes a reaction for producing a compound other than the target substance by branching off from the biosynthetic pathway of the target substance or an enzyme that imports the target substance into cells from the medium may be decreased or eliminated. When the target substance is L-lysine, examples of such an enzyme that catalyzes a reaction for producing a compound other than L-lysine by branching off from the biosynthetic pathway of L-lysine includes homoserine dehydrogenase (refer to WO95/23864). Further, examples of an enzyme that imports L-lysine into cells include lysine permease (lysI gene product).

Examples of the coryneform bacterium in which activity of the target enzyme is reduced or eliminated include, for example, gene-disrupted strains in which a gene of a target enzyme on a chromosome is disrupted by a genetic recombination technique, and mutant strains in which a target enzyme having an activity is no longer produced due to a mutation in an expression regulatory sequence or coding region of the target enzyme gene on a chromosome.

The mutant strains can be obtained by treating a coryneform bacterium with ultraviolet ray irradiation, or a mutagenesis agent which is conventionally used in mutation treatments such as N-methyl-N'-nitro-N-nitrosoguanidine (NTG) or EMS.

Hereinafter, disruption of lysI gene will be explained as an example of the method for disrupting a target enzyme gene on a chromosome by a gene recombination technique. The lysI gene on the chromosome can be disruted by transforming a bacterium belonging to the genus *Escherichia* with a DNA including the lysI gene modified so as not to produce lysine permease, and which has the enzymatic activity (deletion-type lysI gene) by deleting a part of the lysI gene and allowing recombination between the deletion-type lysI gene and the lysI gene on the chromosome. Such gene destruction by homologous recombination has already been established, and there are methods using a linear DNA, a plasmid including a temperature-sensitive replication regulatory region, and so forth.

The lysI gene on the host chromosome can be replaced with the deletion type-lysI gene as follows. For example, recombinant DNA can be prepared by inserting a mutant lysI gene and a marker gene showing resistance to a drug such as kanamycin to an appropriate vector. Then, a coryneform bacterium is transformed with the recombinant DNA, and the transformant strain is cultured in a medium containing the drug to obtain a transformant strain incorporating the recombinant DNA into a chromosomal DNA.

Recombination of the chromosomal lysI gene and the newly inserted recombinant DNA occurs in the strain when inserted as described above. As a result, the two fusion genes containing the chromosomal lysI gene and the deletion-type lysI gene are inserted into the chromosome on both sides of the other part of the recombinant DNA, i.e. the vector portion, temperature-sensitive replication control region and drug resistance marker. Therefore, the transformant strain expresses a normal lysI product, since the normal lysI gene is dominant in this state. Further, if a sucrase gene is incorporated into the recombinant DNA, for example, the recombinant strain expresses sucrase, and hence cannot grow in a medium containing sucrose as a carbon source. Therefore, this gene can be used as the marker.

Subsequently, in order to maintain only the deletion type-lysI gene on the chromosomal DNA, one copy of lysI gene is eliminated from the chromosomal DNA along with the vector segment (including the marker gene) by recombination of two lysI genes (second recombination). At this stage, there is the case where the native lysI gene is left on the chromosomal DNA and the deletion type-lysI gene is eliminated from the chromosomal DNA, or conversely, the case where the deletion-type lysI gene is left on the chromosomal DNA, and the native lysI gene is eliminated from the chromosomal DNA. Therefore, by confirming structures of the gene, there can be obtained a strain in which the deletion-type lysI gene is left on the chromosome.

The aforementioned genes encoding enzymes involved in biosynthesis of target substance can also be introduced into a coryneform bacterium by substitution for a gene on a chromosomal DNA of the coryneform bacterium in the same manner as that for the aforementioned gene disruption.

A target substance can be produced by culturing the coryneform bacterium of the present invention obtained as described above in a medium containing methanol, resulting in accumulation of the target substance in the medium or cells of the bacterium and collecting the target substance from the medium or the cells of the bacterium.

Examples of the target substances which are applicable in the method of the present invention include, but are not limited to, substances produced by metabolism of methanol and substances produced by utilizing energy generated by metabolism of methanol. Specifically, for example, amino acids such as glutamic acid, lysine, threonine, phenylalanine and tryptophan, vitamins such as vitamin C, macromolecular substances such as various kinds of enzymes and so forth are encompassed.

The expression "ability to produce a target substance" used in the present invention means an ability of the coryneform bacterium of the present invention to cause accumulation the target substance in a medium or cells of the bacterium in such an amount that the substance can be collected therefrom, when the bacterium is cultured in the medium under suitable conditions.

In the present invention, the medium and culture conditions may be suitably selected depending on the bacterial strain or the target substance. That is, typical media containing a nitrogen source, inorganic ions, and other organic trace nutrients as required can be used.

Methanol can be used as a carbon source. A particularly preferred culture medium will contain methanol as the primary carbon source, for example, methanol makes up more than 50%, preferably more than 70%, more preferably more than 90%, of the total carbon source. Together with methanol, saccharides such as glucose, lactose, galactose, fructose and starch hydrolysate, alcohols such as glycerol and sorbitol, or organic acids such as fumaric acid, citric acid and succinic acid can be used.

Inorganic ammonium salts such as ammonium sulfate, ammonium chloride and ammonium phosphate, organic nitrogen such as soybean protein hydrolysate, ammonia gas, aqueous ammonia and so forth can be used as the nitrogen source.

Potassium phosphate, magnesium sulfate, iron ion, manganese ion and so forth can be used as inorganic ions or a source thereof in small amounts. It is preferable to add required substances such as L-homoserine and vitamin B1, yeast extract and so forth as organic trace nutrients in suitable amounts as required.

The culture may be preferably carried out under conditions suitable for the coryneform bacterium. Usually, the culture is preferably carried out under an aerobic condition for 16–96 hours. The culture temperature is preferably controlled to be between 20° C. to 45° C., and pH is preferably controlled to be between 5 to 8.5 during the culture. Inorganic or organic, acidic or alkaline substances as well as ammonia gas and so forth can be used to adjust the pH. If a thermophilic bacterium is used as a host, it can be cultured between 42° C. to 60° C.

For collection of the metabolic product from the medium after completion of the culture, any special method is not required for the present invention. That is, it can be carried out by a combination of well-known techniques such as ion exchange resin methods, precipitation methods, and other known method. In addition, when methanol is used as the carbon source, purification of the target substance and waste solution disposal process may be simplified as compared with a case of using sugars derived from agricultural products.

EXAMPLES

Hereinafter, the present invention is explained more specifically with reference to the following non-limiting examples.

Example 1

Cloning of Methanol Dehydrogenase Gene

Chromosomal DNA was prepared in a conventional manner from *Bacillus brevis* S1 strain (NCIMB 12524, obtained from NCIMB), which is a methanol-assimilating high-temperature resistant bacterium belonging to the genus *Bacillus*. Then, a MDH gene was cloned by PCR using this DNA as a template (see Japanese Patent Laid-open Publication No. 2000-69976). MDH-BM-1 (SEQ ID NO: 1) and MDH-BM-2 (SEQ ID NO: 2) were used as primers. These were prepared by referring to the previously reported nucleotide sequence of the MDH gene of *Bacillus methanolicus* C1 strain (registered at GenBank under Accession M65004, entry name of BACMDH). PCR was performed using Pyrobest (Takara Shuzo), and a heat treatment at 94° C. for 90 seconds, followed by reactions at 98° C. for 10 seconds, 55° C. for 30 seconds and 70° C. for 4 minutes repeated for 30 cycles, and further followed by incubation at 72° C. for 10 minutes. A DNA fragment of the desired size was obtained by these reactions.

After this DNA fragment was purified and both ends were blunt-ended, the DNA fragment was cloned into a SmaI site of a shuttle vector pBC4 (described herein) comprising the replication origin derived from pHSG399 (Takara Shuzo) and the replication origin derived from pHM 1519 (described herein). Competent cells of the *E. coli* JM 109 strain (Takara Shuzo) were transformed with the ligation reaction mixture according to the manufacturer's protocol, and several chloramphenicol resistant colonies were subsequently selected. Plasmid DNAs were extracted from these colonies, and their structures were analyzed. A plasmid in which the direction of the mdh gene incorporated into the plasmid is reverse as compared to the direction of the lac promoter of the vector was designated pBC-m-2 and used for the following experiments.

pBC4 was prepared as follows. The plasmid pHK4 (refer to Japanese Patent Laid-open Publication No. 5-7491) having the replication origin derived from the already obtained plasmid pHM1519 (Agric. Biol. Chem., 48, 2901–2903 (1984)) autonomously replicable in coryneform bacteria was digested with the restriction enzymes BamHI and KpnI to obtain a gene fragment containing the replication origin, and the obtained fragment was blunt-ended using DNA Blunting Kit (Takara Shuzo) and inserted into pHSG399 (Takara Shuzo) at the BamHI site by ligation using a BamHI linker (Takara Shuzo). Competent cells of *E. coli* JM109 strain (Takara Shuzo) were transformed with the ligation reaction mixture according to the manufacturer's protocol, and several chloramphenicol resistant colonies were selected. Plasmids were prepared from the resulting colonies as described above to obtain pBC4.

Example 2

Cloning of Gene Encoding MDH Activator (Amd) Derived from *Bacillus subtilis*

It is known that there are factors for activating enzymatic activity of NAD-dependent type methanol dehydrogenases derived from methanol-assimilating bacteria belonging to the genus *Bacillus*. Japanese Patent Laid-open Publication No. 2000-69976 discloses that one of such factors exists in *Bacillus subtilis*. This factor was designated as Amd (Activator of methanol dehydrogenase).

The gene encoding Amd (amd) was cloned from *Bacillus subtilis* in a conventinal manner. Specifically, the cloning was carried out as follows. *Bacillus subtilis* 168 strain was cultured in LB medium, and chromosomal DNA was extracted from the obtained cells in a conventional manner (Biochem. Biophys. Acta., 72, 619–629 (1963)). PCR was performed using the chromosomal DNA as a template and oligonucleotides designed so that the target DNA fragment has EcoRi restriction enzyme sites on both ends (SEQ ID NOS: 11 and 12) to amplify a gene DNA fragment containing amd, which was the target gene. For the amplification, a cycle of a denaturation step at 98° C. for 10 second, an annealing step at 55° C. for 30 second and an extension step at 72° C. for 2 minutes was repeated for 30 cycles. The enzyme used was Pyrobest DNA polymerase (Takara Shuzo), and it was used according to the manufacturer's instruction.

The amplified DNA fragment was purified by phenol/chloroform treatment and ethanol precipitation and then digested with the restriction enzyme EcoRI to prepare an amd fragment having EcoRI sites at the both ends. Separately, pVK7, which is a shuttle vector for *Escherichia coli* and *Corynebacterium glutamicum*, was similarly treated with a restriction enzyme EcoRI. After the phosphate groups at the ends were removed using an alkaline phosphatase, it was ligated to the aforementioned amd fragment. Competent cells of *E. coli* JM 109 strain (Takara Shuzo) were transformed with the ligation reaction mixture according to the manufacturer's protocol, and several kanamycin resistant colonies were selected.

The aforementioned pVK7 was constructed (see Japanese Patent Laid-open Publication No. 10-266881, WO99/07853) by ligating pAM330, which is a cryptic plasmid of *Brevibacterium lactofermentum*, to pHSG299, which is a vector for *Escherichia coli* ($Km^r$, refer to Takeshita, S. et al., Gene, 61, 63–74, (1987)), as follows. pAM330 was prepared from the *Brevibacterium lactofermentum* ATCC 13869 strain. pHSG299 was digested with AvaII (Takara Shuzo), blunt-ended with T4 DNA polymerase, and then ligated to pAM330 digested with HindIII (Takara Shuzo) and blunt-ended with T4 DNA polymerase. Thus, pVK7 was obtained. pVK7 is autonomously replicable in cells of *E. coli* and *Brevibacterium lactofermentum*, and contains a multiple cloning site derived from pHSG299, lacZ' and kanamycin resistance gene as a marker.

Plasmid DNA was extracted from these colonies and analyzed for structure. Then, plasmids containing the amd gene in the same direction as the direction of the lac promoter in the vector was designated as pVK-a and used for the following experiments.

Example 3

Cloning of hps Gene and phi Gene from Methanol-assimilating Bacterium Belonging to the Genus *Bacillus*

Chromosomal DNA was prepared from *Bacillus brevis* S1 strain, which is a methanol-assimilating bacterium belonging to the genus Bacillus, in the same manner as described above. This chromosomal DNA was used as a template in PCR to amplify the target DNA region. The sequences of oligonucleotide primers for PCR (SEQ ID NOS: 13 and 14) were designed so that KpnI restriction enzyme sites is introduced at both ends of the amplified DNA fragment. PCR was performed using Pyrobest (Takara Shuzo), and a heat treatment at 94° C. for 90 seconds, followed by reactions at 98° C. for 10 seconds, 55° C. for 30 seconds and 72° C. for 2 minutes repeated for 25 cycles and subsequent incubation at 72° C. for 10 minutes. Then, the obtained DNA fragment was purified in a conventional manner and treated with a restriction enzyme KpnI to prepare the target DNA having KpnI-digested ends at both ends.

Separately, pVK7, which is a shuttle vector for *Escherichia coli* and *Corynebacterium glutamicum*, was treated with a restriction enzyme KpnI, then treated with an alkaline phosphatase and ligated with the aforementioned DNA fragment using T4 ligase (Takara Shuzo). The *E. coli* JM109 strain was transformed with the ligation mixture in the same manner as described above to obtain many kanamycin resistant colonies. Several colonies were selected, and plasmids harbored by them were investigated to select one in which the target genes hps and phi existed in the same direction as that of the lac promoter on the vector. This plasmid was designated as pVK-h.

Example 4

Construction of Plasmid Containing hps, phi and amd

The plasmids pVK-a and pVK-h produced in Examples 2 and 3 were each treated with restriction enzymes ClaI and SacI. From pVK-a, a smaller DNA fragment containing the amd gene was prepared. Concurrently, a larger DNA fragment containing the hps and phi genes was prepared from pVK-h in a conventional manner and ligated with the amd gene fragment using T4 ligase.

Competent cells of *E. coli* JM109 strain were transformed with the above reaction mixture. Kanamycin-resistant transformants were selected. From several tens of colonies which emerged on an agar plate, 6 colonies were arbitrarily selected, and the structures of plasmids contained within were analyzed. As a result, it was confirmed that all the plasmids had the intended structure, i.e., a structure in which the three kinds of genes, amd, hps, and phi, were carried on the vector pVK7. This plasmid was designated as pVK-ha.

Example 5

Preparation of *Corynebacterium glutamicum* Imparted with an Ability to Utilize Methanol, and an Assay of this Ability The two kinds of plasmids constructed by the methods described in Examples 1 and 4, i.e., pBC-m-2 and pVK-ha, were introduced into *Corynebacterium glutamicum* (ATCC 13869) by electroporation (Gene Pulser produced by BIO-RAD was used, distance between electrodes of cuvette was 0.1 cm, and electric pulse application conditions were 25 μF, 200 Ω and 1.8 kV). The obtained transformants could be selected on a CM-2S agar plate (see below for the composition of the medium) containing 5 μg/l of chloramphenicol and 25 μg/l of kanamycin. The transformants were cultured overnight at 31.5° C. with shaking in the CM-2S liquid medium containing 5 μg/l of chloramphenicol and 25 μg/l of kanamycin. The culture was performed in 3 ml of culture broth using a test tube.

The CM-2S medium was prepared as follows. All the components shown in Table 1 were mixed, adjusted to pH 7.2 with KOH and then sterilized by autoclaving at 120° C. for 20 minutes. In the case of an agar medium, 20 g/L of agar was added.

| Composition of CM-2S medium (per 1 L) | |
|---|---|
| Sucrose | 5 g |
| Polypeptone | 10 g |
| Yeast extract | 10 g |
| NaCl | 5 g |
| DL-Methionine | 0.1 g |
| (Filled up to 1 L with sterilized water) | |

Then, the aforementioned culture broth, following the overnight culture, was inoculated into 1% (v/v) to the MM-MES-RC medium (see below for the medium composition), added with unlabeled methanol to a final concentration of 0.2% (v/v), and culture was performed at 31.5° C. for about 40 hours with shaking. During the culture, the methanol concentration in the medium was measured over time using gas chromatography. The culture in the medium containing methanol was performed in 10 ml of culture broth using an L-shaped test tube. Further, as a control that lacked methanol dehydrogenase enzyme and therefore evidently lacked the ability to utilize methanol, *Corynebacterium glutamicum* (ATCC 13869) introduced only with pVK-ha by electroporation was also cultured under the same conditions, and the change of methanol concentration in the medium over the period of time was similarly observed.

The MM-MES-RC medium was prepared as follows. The components other than D-ribose and casamino acid were mixed to prepare a solution having a 5-fold higher concentration, and the solution was adjusted to pH 7.0 with NaOH and subjected to filter sterilization. Further, aqueous solutions containing each of 50% of D-ribose and 10% of casamino acid were prepared and subjected to filter sterilization. Then, upon actual use, the 50% D-ribose solution and the 10% casamino acid solution were added so that the both substances have a final concentration of 5 g/L, 200 ml of the solution having a 5-fold higher concentration was further added, and filled up to a final volume of 1 L with sterilized water.

TABLE 2

| Composition of MM-MES-RC medium (per 1 L) | |
|---|---|
| D-Ribose | 5 g |
| Casamino acid | 5 g |
| $(NH_4)_2SO_4$ | 10 g |
| $KH_2PO_4$ | 1 g |
| $MgSO_4.7H_2O$ | 0.4 g |
| $FeSO_4.7H_2O$ | 0.01 g |
| $MnSO_4.4\text{-}5H_2O$ | 0.01 g |
| Vitamin $B_1$.HCl | 200 μg |

TABLE 2-continued

| Composition of MM-MES-RC medium (per 1 L) | |
|---|---|
| Biotin | 50 μg |
| Nicotinamide | 5 mg |
| NaCl | 1 g |
| MES (0.1 M) | 19.5 g |
| (Filled up to 1 L with sterilized water) | |

MES: 2-(Morpholino)ethanesulfonic acid

As a result, it was confirmed that the decreasing rate of methanol in the medium of the strain harboring both pBC-m-2 and pVK-ha was significantly higher than the decreasing rate of methanol in the medium of the strain introduced only with pVK-ha. It was considered that, in this experiment, the decrease of methanol in the medium observed for the strain introduced only with pVK-ha that could not consume methanol was caused by natural evaporation since it did not have methanol dehydrogenase. Therefore, the result that the strain harboring both of pBC-m-2 and pVK-ha decreased methanol in the medium more quickly suggested that the strain acquired an ability to consume methanol.

Example 6

Construction of L-lysine-producing Strain of *Corynebacterium glutamicum*

*Corynebacterium glutamicum* modified so as to be able to produce L-lysine was constructed by the method described below. *Corynebacterium glutamicum* (ATCC 13869) was used as a parent strain. The aspartokinase gene (lysC) on the chromosome of the strain was replaced with a mutant lysC gene (lysC*) encoding the aspartokinase for which inhibition is desensitized. The mutant lysC gene was identified in the lysine producing bacterium (AJ3463). Moreover, the lysine permease gene (lysI) was modified into an inactive type lysI gene by deleting a part thereof. Specifically, the following experimental operations were performed.

First, the cryptic plasmid pAM330 harbored by the parent strain, *Corynebacterium glutamicum* (ATCC 13869), was eliminated in a conventional manner. Then, a plasmid pBS3C* for changing the lysC gene into the lysC* gene was constructed by the method described below. pHSG299 (Takara Shuzo) was digested with the restriction enzyme AvaII, both ends were blunt-ended with DNA Blunting Kit (Takara Shuzo) and dephosphorylated with alkaline phosphatase, and the resulting fragment was ligated to a DNA fragment containing the sacB gene (levan sucrase gene of *Bacillus subtilis*) using T4 DNA ligase. This DNA fragment containing the sacB gene was obtained by PCR using chromosome of the *Bacillus subtilis* 168 strain extracted in a conventional manner as a template and Primer 3 (SEQ ID NO: 3) and Primer 4 (SEQ ID NO: 4) (Pyrobest (Takara Shuso). The reaction of a heat treatment at 94° C. for 90 seconds, followed by reactions at 98° C. for 10 seconds, 55° C. for 30 seconds and 72° C. for 1.5 minutes repeated 25 cycles, and further followed by incubation at 72° C. for 10 minutes) was conducted. The amplified product was digested with the restriction enzymes BglII and BamHI, and both ends blunt-ended with DNA Blunting Kit (Takara Shuzo).

Competent cells of the *Escherichia coli* JM 109 strain were transformed with the ligation reaction mixture. Then, kanamycin-resistant transfromants were selected. A plasmid was extracted from a transformant in which introduction of the sacB gene into pHSG299 was confirmed as designed among the emerged colonies, and the obtained plasmid was designated as pBS3.

Then, both of the pBS3 and p399AK9 (described in WO94/25605, a plasmid consisting of pHSG399 (Takara Shuzo) carrying the lysC* gene of the L-lysine-producing bacterium, AJ3463 strain) were digested with the restriction enzymes EcoRI and SphI. The region containing the sacB gene and the region containing the lysC* gene were ligated using T4 DNA ligase. Competent cells of *Escherichia coli* JM109 strain were transformed with the ligation mixture. Then, the kanamycin-resistant transformants were selected. Plasmids harbored by the obtained transformants were prepared and their structures confirmed. A plasmid in which the lysC* gene derived from p399AK9 was inserted into pBS3 as designed was selected. This plasmid was designated as pBC3C*.

The wild-type lysC gene in a *Corynebacterium glutamicum* (ATCC 13869 strain) having pAM330 eliminated was replaced with the lysC* gene using pBC3C* by the following procedures. First, pBC3C* was introduced into the ATCC 13869 strain in a conventional manner to obtain a strain that could grow in the CMDex medium (see below for the composition) containing 10 μg/ml of kanamycin. Since pBC3C* did not contain any replication origin replicable in the ATCC 13869 strain, the obtained strain exhibiting kanamycin resistance is the ATCC 13869 strain in which the lysC* gene of pBC3C* was incorporated into the lysC gene region on a chromosome of the ATCC 13869 strain by homologous recombination. Then, this strain that had undergone recombination once was cultured overnight at 31.5° C. in the CMDex medium and then applied on the DX-S10 agar medium (see below for the composition). During the culture, a second recombination occurred at the lysC region, and a strain in which the vector segment containing the sacB gene region of pBC3C* was eliminated was selected as a strain that could grow on agar medium and exhibit the kanamycin sensitivity. If the sacB gene remains on the chromosome, the strain cannot grow in the DX-S10 medium containing sucrose due to the activity of sucrase, which is the product of the gene. The nucleotide sequences of the lysC gene regions of the candidate strains obtained as described above were determined in a conventional manner, and a strain in which substitution of lysC* gene was confirmed was designated as a 2256C* strain.

The CMDex medium was prepared as follows. All the components shown in Table 3 were mixed, adjusted to pH 7.5 with KOH and then sterilized by autoclaving at 120° C. for 20 minutes. In the case of an agar medium, agar was added at a final concentration of 20 g/L.

Further, the DX-S10 agar medium was prepared as follows. All the components shown in Table 4 were mixed, adjusted to pH 7.5 with KOH and then sterilized by autoclaving at 120° C. for 20 minutes. Then, 200 ml of 50% sucrose subjected to filter sterilization was added.

TABLE 3

| Composition of CMDex medium (per 1 L) | |
|---|---|
| Glucose | 5 g |
| Polypeptone | 10 g |
| Yeast extract | 10 g |
| $KH_2PO_4$ | 1 g |
| $MgSO_4.7H_2O$ | 0.4 g |
| $FeSO_4.7H_2O$ | 0.01 g |
| $MnSO_4.4\text{-}5H_2O$ | 0.01 g |
| Urea | 3 g |

TABLE 3-continued

| Composition of CMDex medium (per 1 L) | |
|---|---|
| Mameno* (in terms of nitrogen weight) | 1.2 g |
| Biotin | 10 μg |
| (Filled up to 1 L with sterilized water) | |

*soybean protein hydrolysate

TABLE 4

| DX-S10 agar medium composition except for sucrose (per 1 L) | |
|---|---|
| Polypeptone | 10 g |
| Yeast extract | 10 g |
| $KH_2PO_4$ | 1 g |
| $MgSO_4.7H_2O$ | 0.4 g |
| $FeSO_4.7H_2O$ | 0.01 g |
| $MnSO_4.4–5H_2O$ | 0.01 g |
| Urea | 3 g |
| Mameno (in terms of nitrogen weight) | 1.2 g |
| Biotin | 10 μg |
| Agar powder | 18 g |
| (Filled up to 800 mL with sterilized water) | |

Further, for disruption of the lysI gene, a plasmid pBS3IΔ was constructed as follows. A first DNA fragment was amplified by PCR using a chromosomal DNA obtained from *Corynebacterium glutamicum* in a conventional manner as a template and Primer 5 (SEQ ID NO: 5) and Primer 6 (SEQ ID NO: 6). Separately, a second DNA fragment amplified by PCR using a chromosomal DNA obtained from *Corynebacterium glutamicum* in a conventional manner as a template and Primer 7 (SEQ ID NO: 7) and Primer 8 (SEQ ID NO:8). PCR was performed using LA-taq (Takara Shuzo) and heat treatment at 94° C. for 5 seconds, followed by reactions at 94° C. for 30 seconds, 52° C. for 30 seconds and 72° C. for 1 minute, and repeated for 25 cycles, followed by subsequent incubation at 72° C. for 10 minutes. Then, the first and the second DNA fragments obtained as described above were used as templates with Primer 9 (SEQ ID NO:9) and Primer 10 (SEQ ID NO:10) to perform crossover PCR and thereby obtain a DNA fragment of the lysI gene having a sequence around the center of the coding region deleted (lysIΔ). The 5' end regions of Primer 6 and Primer 7 were designed to have sequences complementary to each other so that they anneal. The crossover PCR was performed using LA-taq (Takara Shuzo), and a heat treatment at 94° C. for 5 seconds, followed by reactions at 94° C. for 30 seconds, 52° C. for 30 seconds and 72° C. for 1 minute for 25 cycles and followed by subsequent incubation at 72° C. for 10 minutes.

Then, both the DNA fragment (lysIΔ) obtained as described above and the plasmid pBS3 (described above in Example 6) were digested with the restriction enzyme XbaI and ligated using T4 DNA ligase. Competent cells of *Escherichia coli* JM109 strain was transformed with the ligation mixture. The kanamycin-resistant transformants were selected. Plasmids were collected from the transformants, and their structures were confirmed. As a result, a plasmid in which a DNA fragment of the lysI gene of which partial sequence was deleted was inserted into pBS3 as designed was obtained and designated as pBC3IΔ.

Then, the lysI gene of the *Corynebacterium glutamicum* 2256C* strain was inactivated by the following procedures using pBC3IΔ. First, pBC3IΔ was introduced into the 2256C* strain in a conventional manner, and a strain that could grow in the CMDex medium containing 10 μg/ml of kanamycin was obtained. Since pBC3IΔ did not contain any replication origin replicable in the 2256C* strain, the obtained strain exhibiting the kanamycin resistance is the 2256C* strain in which the lysIΔ region of pBC3IΔ was incorporated into the lysI region of the 2256C* strain by homologous recombination. Then, this strain that had undergone recombination once was cultured overnight at 31.5° C. in the CMDex medium and then applied on the DX-S10 agar medium. During the culture, a second recombination occurred between the lysI gene on a chromosome and the lysIΔ region in this strain, and a strain in which the vector segment containing the sacB gene region of pBC3IΔ was eliminated could grow on the agar medium and become kanamycin-sensitive. This is because if the sacB gene remains on the chromosome, the strain cannot grow in the DX-S10 medium also containing sucrose due to the activity of sucrase, the product of the gene. Therefore, a strain that could grow on the DX-S10 agar medium and was kanamycin-sensitive was selected as a strain that had undergone recombination twice. The lysI gene internal region of the obtained strain that had undergone recombination twice was amplified by PCR using Primer 9 (SEQ ID NO:9) and Primer 10 (SEQ ID NO:10), and a strain having lysI gene confirmed to be shorter than the wild-type lysI gene, was used as a lysI-deficient strain.

By the aforementioned procedures, strains in which the lysC gene was replaced with the lysC* gene, and thus the lysI gene was deleted, could be obtained, and one strain among them was designated a 2256CI strain (AJ110135 strain). This strain could grow by utilizing a saccharide as a carbon source and could produce L-lysine in the medium as described in Example 8.

Example 7

Introduction of mdh, amd, hps and phi into L-lysine-producing Strain of *Corynebacterium glutamicum* pBC-m-2 and pVK-ha constructed in Example 1 and Example 2 were introduced in a conventional manner into the *Corynebacterium glutamicum* AJ 110135 strain modified so that it produces L-lysine. The AJ110135 strain harboring these two kinds of plasmids contain all the genes of mdh, amd, hps and phi. This strain harboring the plasmids was designated as MCL101 strain. When this strain was cultured as a usual operation, it was cultured at 31.5° C. with shaking in the CM-2S medium containing antibiotics kanamycin and chloramphenicol at concentrations of 25 μg/L and 10 μg/L, respectively.

Example 8

Assay of Ability to Utilize Methanol of Lysine-producing Bacterium, *Corynebacterium glutamicum* MCL101 Strain, Introduced with mdh, amd, hps and phi It was examined whether the MCL101 strain constructed in Example 7 could utilize methanol in a medium as a carbon source. The MCL101 strain was cultured overnight at 31.5° C. with shaking in the CM-2S medium containing 25 μg/L of kanamycin and 10 μg/L of chloramphenicol. This culture broth was inoculated in an amount of 1% (v/v) to the MM-MES-RC medium containing 25 μg/L of kanamycin and 10 μg/L of chloramphenicol and added with $^{13}C$-labeled methanol at a final concentration of 0.2% (v/v) and the MM-MES-RC medium added with unlabeled methanol at a final concentration of 0.2% (v/v) and cultured at 31.5° C. for 50 hours with shaking. After the culture, absorbance of both culture broths was measured at 660 nm, which represented the degree of growth. The absorbance reached about 1.7 in the both culture broths, and any significant difference in growth of the bacterium was not observed between the two strains. Moreover, when the methanol concentration after the culture of both culture broths was measured by gas chromatography, it was confirmed that substantially equal amounts of methanol was consumed in both culture broths. Then, both culture broths were centrifuged (8000 rpm for 15 minutes) to prepare culture supernatants, and they were lyophilized.

60 mg of each lyophilized powder obtained from the supernatants of both culture broths was dissolved in 500 μl of heavy water. The L-lysine amount in each solution was measured, and it was found to be about 1.3 mg in the each solution, and the amounts of L-lysine in the each solution were substantially the same. Then, each solution was subjected to $^{13}$C-NMR to analyze the ratio of $^{13}$C in the carbon atoms constituting the produced L-lysine molecules. As a result, the signal of each carbon atom of L-lysine produced by the culture containing $^{13}$C-labeled methanol was about 3.3 to 9.9 times stronger than that of L-lysine produced by the culture with unlabeled methanol. This result indicates that the constructed MCL101 strain newly acquired an ability to take up the $^{13}$C-labeled methanol added to the medium and utilize it even for L-lysine production, and this further indicates that a coryneform bacterium imparted with an ability to utilize methanol could be constructed.

While the invention has been described with reference to preferred embodiments thereof, it will be apparent to one skilled in the art that various changes can be made, and equivalents employed, without departing from the scope of the invention. Each of the aforementioned documents, including the foreign priority document, JP2003-57171, is incorporated by reference herein in its entirety.

[Explanation of SEQ ID NOS]

SEQ ID NOS: 1 and 2: Primer sequences for cloning mdh

SEQ ID NOS: 3 and 4: Primers for cloning sacB gene

SEQ ID NOS: 5 to 10: Primers for constructing DNA fragment containing lysI gene of which central region is deleted SEQ ID NOS: 11 and 12: Primers for cloning yqkG (amd)

SEQ ID NOS: 13 and 14: Primers for cloning hps-phi

SEQ ID NO: 15: Nucleotide sequence of yqkG (amd) of *Bacillus subtilis* 168 strain SEQ ID NO: 16: Amino acid sequence of yqkG.(amd) of *Bacillus subtilis* 168 strain SEQ ID NO: 17: Nucleotide sequence of hps-phi (S1) of *Bacillus brevis* S1 strain SEQ ID NO: 18: Amino acid sequence of HPS of *Bacillus brevis* S1 strain SEQ ID NO: 19: Amino acid sequence of PHI of *Bacillus brevis* S1 strain

What is claimed is:

1. A method for producing an L-amino acid using a coryneform bacterium comprising:

(A) culturing a coryneform bacterium having an ability to produce said L-amino acid in a medium, resulting in accumulation of the L-amino acid in the medium or cells of the bacterium, and (B) collecting the L-amino acid from the medium or the cells of the bacterium, wherein a methanol dehydrogenase gene, hexulose phosphate synthase gene and phoshohexuloisomerase gene are introduced into said coryneform bacterium, and said bacterium is modified so that an ability to utilize methanol is imparted, and the medium contains methanol as a carbon source, and wherein said methanol dehydrogenase gene is derived from *Bacillus brevis* or *Bacillus methanolicus,* said hexulose phosphate synthase gene is a DNA comprising nucleotides 508 to 1140 of SEQ ID NO: 17 or a DNA that can hybridize with nucleotides 508 to 1140 of SEQ ID NO: 17 under stringent conditions and encodes a protein having hexulose phosphate synthase activity, and said phosphohexuloisomerase gene is a DNA comprising nucleotides 1149 to 1700 in SEQ ID NO: 17 or a DNA that can hybridize with nucleotides 1149 to 1700 of SEQ ID NO: 17 under stringent conditions and encodes a protein having phosphohexuloisomerase activity, wherein said stringent conditions are conditions which allow DNA molecules having 95% homology to hybridize.

2. The method according to claim 1, wherein said bacterium is further introduced with a gene encoding a methanol dehydrogenase activity-promoting factor, wherein said gene encoding a methanol dehydrogenase activity promoting factor is a DNA comprising nucleotides 1 to 555 in SEQ ID NO: 15 or a DNA that can hybridize with nucleotides 1–555 in SEQ ID NO: 15 under stringent conditions and encodes a protein having an activity to promote methanol dehydrogenase activity, wherein said stringent conditions are conditions which allow DNA molecules having 95% homology to hybridize.

3. The method according to claim 1, wherein said L-amino acid is L-lysine.

4. The method according to claim 2, wherein said L-amino acid is L-lysine.

5. The method according to claim 3, wherein said bacterium belongs to the genus *Corynebacterium.*

6. The method according to claim 5, wherein said coryneform bacterium is *Corynebacterium glutamicum.*

7. A coryneform bacterium which is introduced with a methanol dehydrogenase gene, hexulose phosphate synthase gene and phosphohexuloisomerase gene, and wherein said bacterium is modified so that an ability to utilize methanol is imparted, wherein said methanol dehydrogenase gene is derived from *Bacillus brevis* or *Bacilus methanolicus*, said hexulose phosphate synthase gene is a DNA comprising nucleotides 508 to 1140 of SEQ ID NO: 17 or a DNA that can hybridize with nucleotides 508 to 1140 of SEQ ID NO: 17 under stringent conditions and encodes a protein having hexulose phosphate synthase activity, and said phosphohexuloisomerase gene is a DNA comprising nucleotides 1149 to 1700 in SEQ ID NO: 17 or a DNA that can hybridize with nucleotides 1149 to 1700 of SEQ ID NO: 17 under stringent conditions and encodes a protein having phosphohexuloisomerase activity, wherein said stringent conditions are conditions which allow DNA molecules having 95% homology to hybridize.

8. The coryneform bacterium according to claim 7, which is further introduced with a gene encoding a methanol dehydrogenase activity promoting factor, wherein said gene encoding a methanol dehydrogenase activity promoting factor is a DNA comprising nucleotides 1 to 555 in SEQ ID NO: 15 or a DNA that can hybridize with nucleotides 1–555 in SEQ ID NO: 15 under stringent conditions and encodes a protein having an activity to promote methanol dehydrogenase activity, wherein said stringent conditions are conditions which allow DNA molecules having 95% homology to hybridize.

9. The coryneform bacterium according to claim 8, which belongs to the genus *Corynebacterium.*

10. The coryneform bacterium according to claim 9, which is *Corynebacterium glutamicum.*

* * * * *